United States Patent
Porat et al.

(10) Patent No.: US 7,383,839 B2
(45) Date of Patent: Jun. 10, 2008

(54) ORAL NASAL CANNULA

(75) Inventors: Ron Porat, D.N. Haela (IL); Joshua Lewis Coleman, Jerusalem (IL); Gershon Levitsky, Jerusalem (IL)

(73) Assignee: Oridion Medical (1987) Ltd., Jerusalem (IL)

( * ) Notice: Subject to any disclaimer, the term of this patent is extended or adjusted under 35 U.S.C. 154(b) by 0 days.

(21) Appl. No.: 11/286,295

(22) Filed: Nov. 22, 2005

(65) Prior Publication Data

US 2006/0130840 A1    Jun. 22, 2006

Related U.S. Application Data

(60) Provisional application No. 60/630,244, filed on Nov. 22, 2004.

(51) Int. Cl.
*A61M 15/08*    (2006.01)
*A61B 5/08*    (2006.01)

(52) U.S. Cl. .................. 128/207.18; 128/DIG. 26; 128/206.11; 600/532

(58) Field of Classification Search ........... 128/201.23, 128/204.18, 206.11, 206.28, 206.29, 207.13, 128/207.18, DIG. 26, 200.24; 606/199, 606/529, 532, 543
See application file for complete search history.

(56) References Cited

U.S. PATENT DOCUMENTS

| | | | | | |
|---|---|---|---|---|---|
| 4,263,908 | A | * | 4/1981 | Mizerak | 128/205.25 |
| 4,454,880 | A | * | 6/1984 | Muto et al. | 128/205.25 |
| 5,046,491 | A | * | 9/1991 | Derrick | 128/200.24 |
| 5,199,421 | A | * | 4/1993 | Figgiani et al. | 128/201.11 |
| 5,375,593 | A | * | 12/1994 | Press | 128/207.18 |
| 6,379,312 | B2 | * | 4/2002 | O'Toole | 600/529 |
| 6,533,983 | B2 | * | 3/2003 | Curti | 264/219 |
| 7,007,694 | B2 | * | 3/2006 | Aylsworth et al. | 128/206.11 |
| 2004/0206907 | A1 | * | 10/2004 | Yamamori et al. | 250/343 |

\* cited by examiner

*Primary Examiner*—Justine R. Yu
*Assistant Examiner*—Shumaya B. Ali
(74) *Attorney, Agent, or Firm*—EMPK & Shiloh, LLP (57) ABSTRACT

There is provided an oral nasal cannula for sampling breath of a subject, including a main body portion, having formed therein a suction port which is adapted to be connected to a suction device for side sampling of exhaled breath of the subject, at least one nasal prong integrally formed with the main body portion and adapted to collect nasally exhaled breath of the subject and an oral scoop, integrally formed with the main body portion and adapted to collect orally exhaled breath of the subject.

20 Claims, 12 Drawing Sheets

ORAL NASAL CANNULA

REFERENCE TO RELATED APPLICATIONS

The present application is related to U.S. Provisional Patent Application Ser. No. 60/630,244 filed Nov. 22, 2004 and entitled ORAL NASAL CANNULA the disclosure of which is hereby incorporated by reference and priority of which is hereby claimed pursuant to 37 CFR 1.78(a) (4) and (5)(i).

FIELD OF THE INVENTION

The present invention relates to the field of oral nasal cannulae for use in sampling the breath of subjects, especially for the purpose of providing capnographic data concerning the subject.

BACKGROUND OF THE INVENTION

The following U.S. Patents are believed to represent the current state of the art:

6,913,017; 6,837,238; 6,655,385; 6,439,234; 6,422,240; 5,794,619; 5,740,799; 5,495,848; 5,375,593; 5,335,656; 5,269,296; 5,046,491; 4,572,177; 4,367,735; 4,156,426; 4,151,843; 4,106,505 and 2,693,800.

SUMMARY OF THE INVENTION

The present invention seeks to provide an improved oral nasal sampling cannula for use with a capnographic system.

There is thus provided in accordance with a preferred embodiment of the present invention an oral nasal cannula for sampling breath of a subject, including a main body portion, having formed therein a suction port which is adapted to be connected to a suction device for side sampling of exhaled breath of the subject, at least one nasal prong integrally formed with the main body portion and adapted to collect nasally exhaled breath of the subject and an oral scoop, integrally formed with the main body portion and adapted to collect orally exhaled breath of the subject.

In accordance with a preferred embodiment of the present invention the main body portion is formed with at least one of at least one oral oxygen delivery port and at least one nasal oxygen delivery port. Preferably, the at least one nasal oxygen delivery port includes a plurality of oxygen delivery holes formed in the main body portion. Alternatively, the at least one nasal oxygen delivery port includes at least one oxygen delivery prong which is integrally formed with the main body portion, which is shorter than the at least one nasal prong and is adapted to be inserted into a nostril of the subject.

In accordance with another preferred embodiment of the present invention, the oral nasal cannula also includes a nasal spacer, adapted to distance the at least one nasal oxygen delivery port from the nose of the subject when the oral nasal cannula is placed on the face of the subject. Preferably, the at least one oral oxygen delivery port is formed over the oral scoop. More preferably, the at least one oral oxygen delivery port is directed sideways, such that delivered oxygen is directed around the oral scoop.

In accordance with yet another preferred embodiment of the present invention, the oral scoop includes an inner surface which is configured to direct breath, exhaled from the mouth of the subject in substantially any direction, toward the suction port. Preferably, the oral scoop covers substantially a majority of the mouth of the subject when the oral nasal cannula is placed on the face of the subject. Additionally or alternatively, the oral nasal cannula is formed with an angle between the at least one nasal prong and the oral scoop. Preferably, the angle is in the range of 145-165 degrees.

In accordance with a further preferred embodiment of the present invention the inner surface includes a plurality of flow surfaces each having a different flow direction.

BRIEF DESCRIPTION OF THE DRAWINGS

The present invention will be understood and appreciated more fully from the following detailed description, taken in conjunction with the drawings in which:

FIGS. 3A, 3B and 3C are schematic illustrations of gas flow in the oral nasal sampling cannula of FIGS. 1A-2B, wherein FIG. 3A depicts oxygen flow and FIGS. 3B and 3C depict sampling of exhaled breath;

FIGS. 6A, 6B and 6C are schematic illustrations of gas flow in the oral nasal sampling cannula of FIGS. 4A-5B, wherein FIG. 6A depicts oxygen flow and FIGS. 6B and 6C depict sampling of exhaled breath;

FIGS. 9A, 9B and 9C are schematic illustrations of gas flow in the oral nasal sampling cannula of FIGS. 7A-8B, wherein FIG. 9A depicts oxygen flow and FIGS. 9B and 9C depict sampling of exhaled breath.

DETAILED DESCRIPTION OF PREFERRED EMBODIMENTS

Figure 1A:
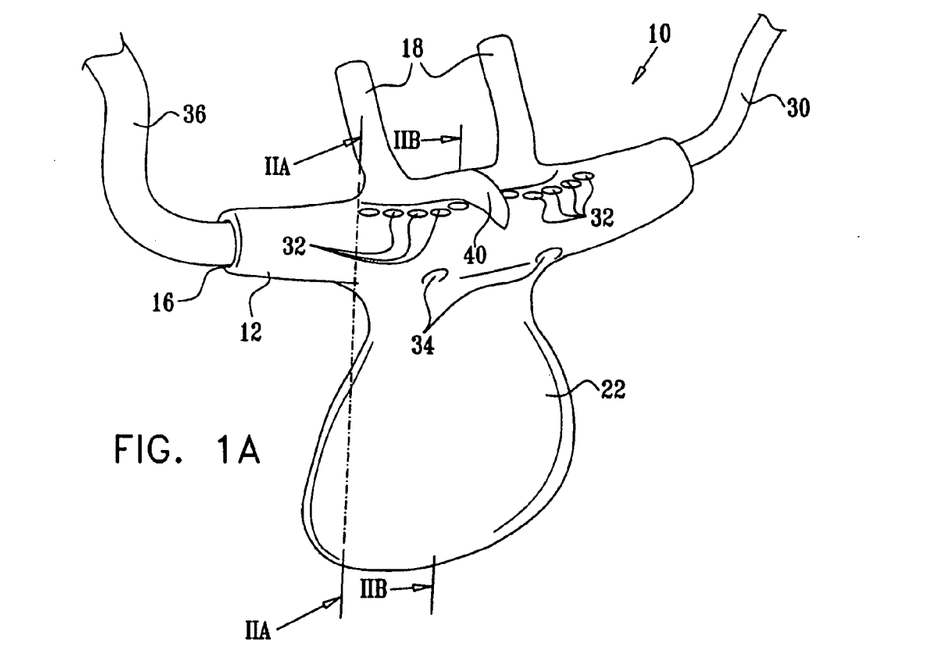
FIGS. 1A and 1B are simplified front-view and rear-view pictorial illustrations of an oral nasal sampling cannula constructed and operative in accordance with a preferred embodiment of the present invention.
Figure 1B:
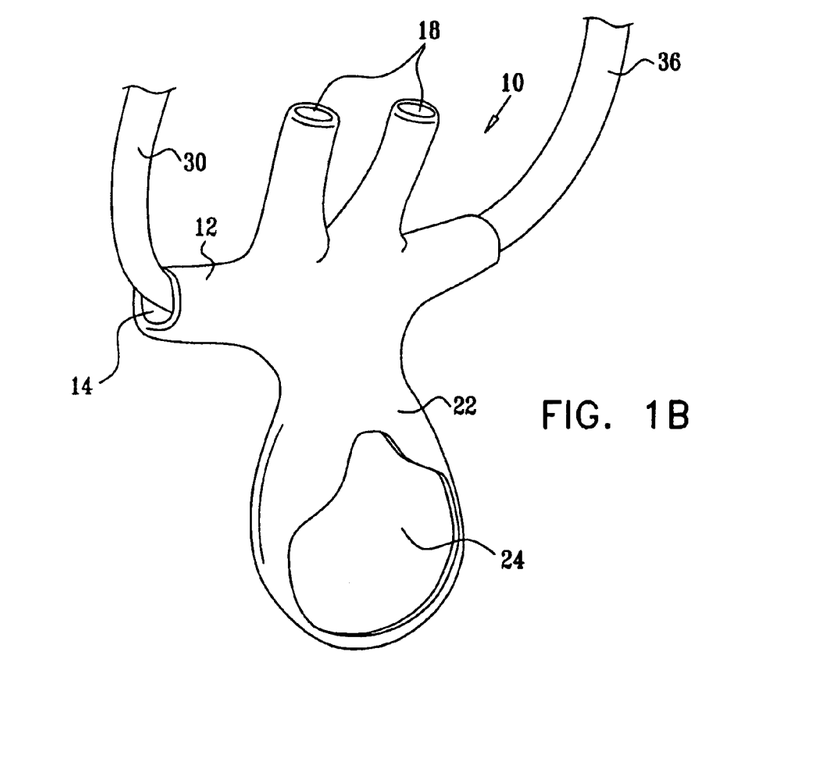
Figure 2A:
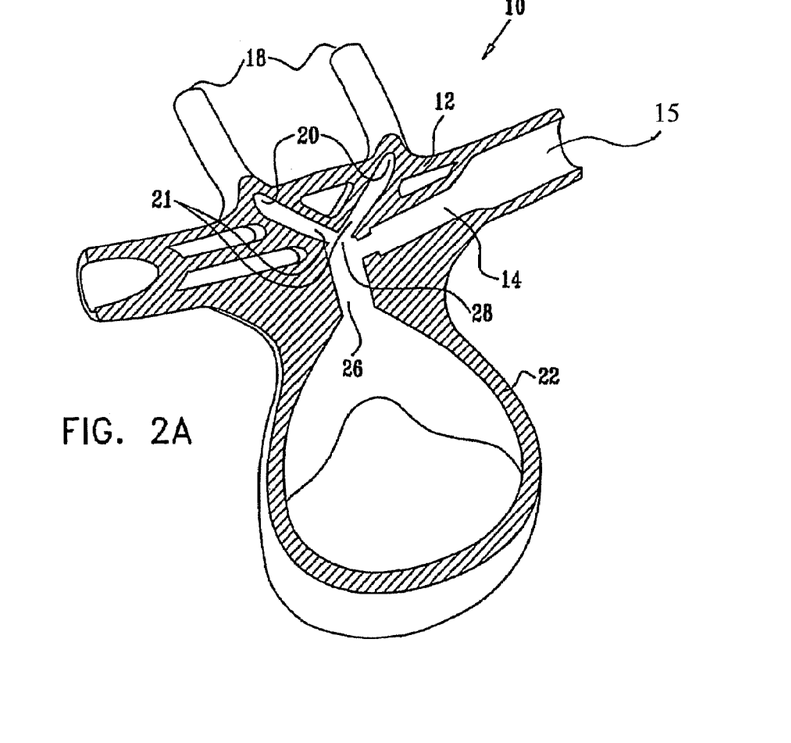
FIGS. 2A and 2B are simplified sectional illustrations taken along section lines IIA-IIA and IIB-IIB in FIG. IA.
Figure 2B:
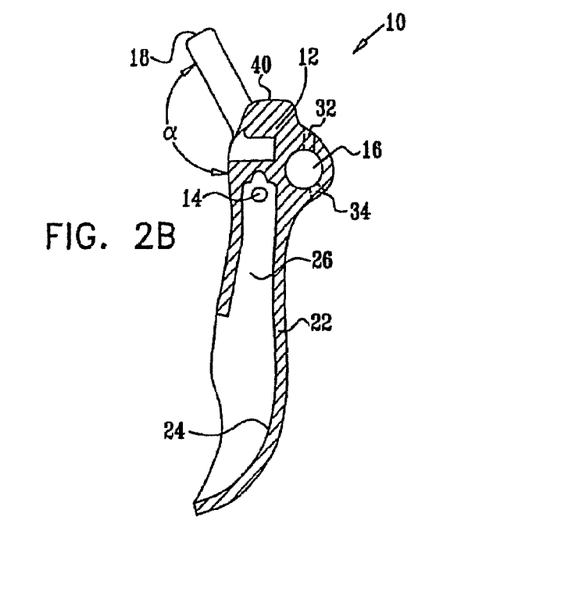

Reference is now made to FIGS. 1A and 1B, which are simplified front-view and rear-view pictorial illustrations of an oral nasal sampling cannula constructed and operative in accordance with a preferred embodiment of the present invention and to FIGS. 2A and 2B, which are simplified sectional illustrations thereof.

FIGS. 1A-2B show an oral nasal sampling cannula 10, which is adapted for collection of gases, such as carbon dioxide, exhaled by a subject, and for supplying oxygen to the subject.

The oral nasal sampling cannula 10 comprises a main body portion 12, having formed therein an exhaled breath collection bore 14 and an oxygen delivery bore 16. A pair of hollow nasal prongs 18, having inner ends 20 which are in fluid flow communication with a pair of nasal breath collection bores 21, is adapted for insertion into the nostrils of the subject and is integrally formed with the main body portion 12.

An oral scoop element 22, including an internal surface 24, is integrally formed with main body portion 12. Oral scoop element 22 terminates at a top portion thereof in an oral breath collection bore 26, which is in fluid flow connection with nasal breath collection bores 21, thereby forming an essentially single junction 28.

Single junction 28 is in fluid flow communication with exhaled breath collection bore 14, which in turn is in fluid flow communication, at suction port 15 with an exhaled breath collection tube 30, which is adapted to be connected to a suctioning pump, such as that used in a side-stream capnograph (not shown), for example Microcap®, which is commercially available from Oridion BreathID of Jerusalem, Israel.

Main body portion 12 includes, preferably at a forward facing surface thereof or alternatively at any other suitable location, nasal oxygen delivery openings 32 and may optionally also include oral oxygen delivery openings 34, both nasal and oral oxygen delivery openings being in fluid flow communication with oxygen delivery bore 16, as seen with particular clarity in FIG. 2B. Oxygen delivery bore 16 is in fluid flow communication with an oxygen delivery tube 36, which is adapted to be connected to a source of oxygen (not shown).

Oxygen delivery tube 36 and exhaled breath collection tube 30 may optionally be placed around the ears of the subject, thereby stabilizing the oral nasal sampling cannula 10 on the subject's face.

As seen clearly in FIG. 1A, a nasal spacer 40 is integrally formed with main body portion 12 at a forward facing surface thereof. Nasal spacer 40 is adapted to engage the nose of the subject, thereby distancing the nose from nasal oxygen delivery openings 32 and ensuring that a sufficient oxygen supply reaches the subject's nose, while not closing off the subject's nasal opening, which would incur a resistance to air flow during exhalation.

Preferably, the oral nasal sampling cannula 10 is suited to the structure of a human face by having an angle, indicated by the letter $\alpha$ in FIG. 2B, between nasal prongs 18 and oral scoop element 22. Angle $\alpha$ is preferably of approximately 145-165 degrees.

Figure 3A:
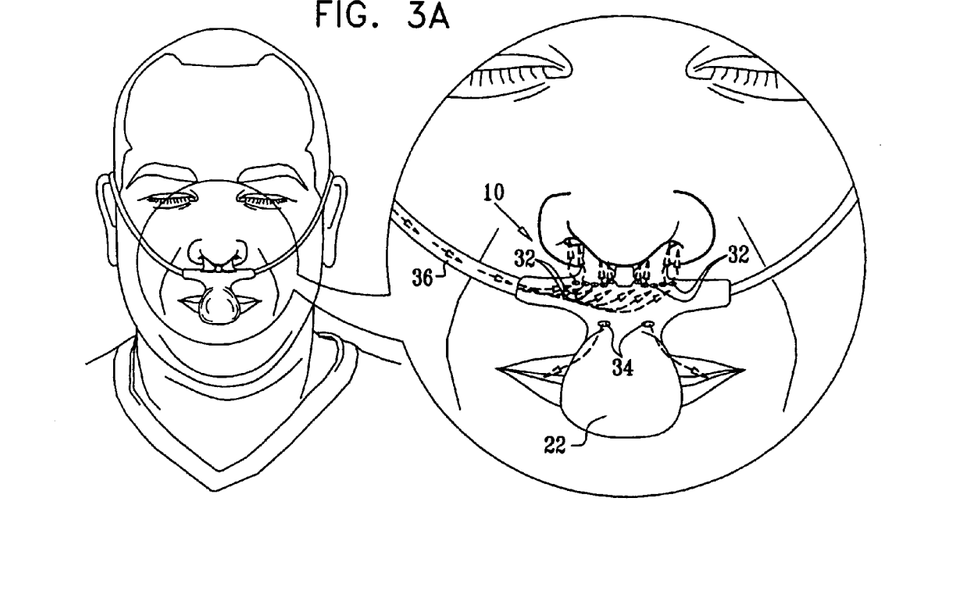
Figure 3B:
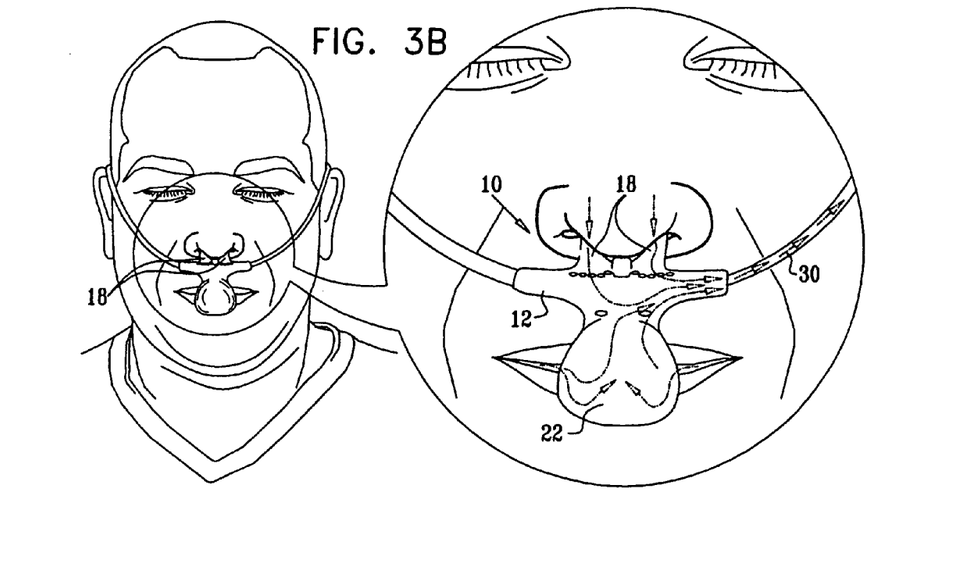
Figure 3C:
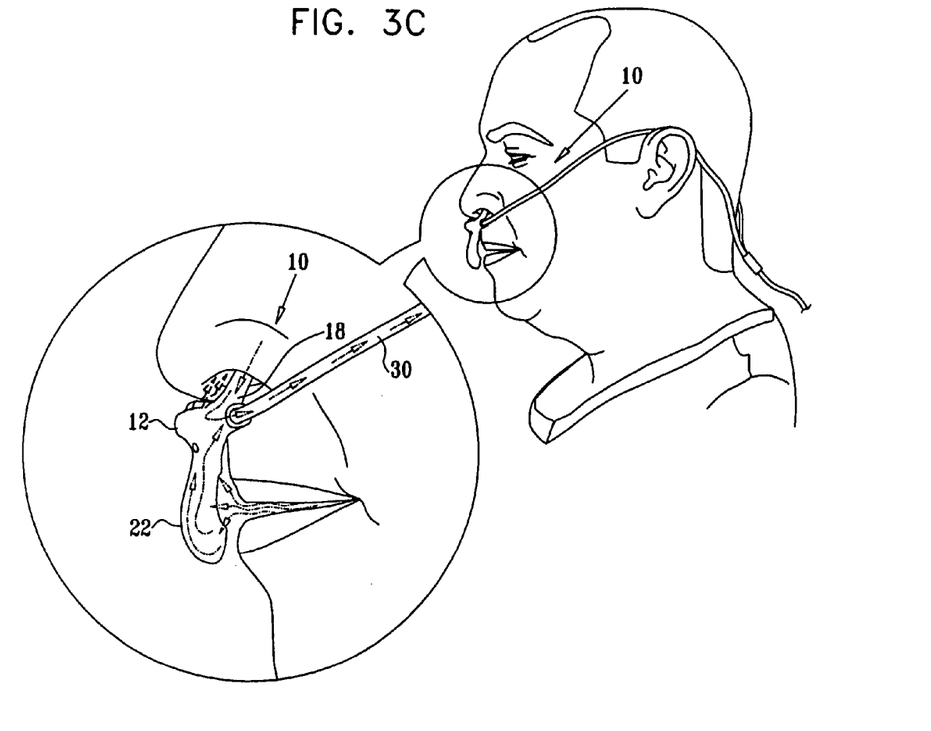

Reference is now made to FIGS. 3A, 3B and 3C, which are schematic illustrations of gas flow in the oral nasal sampling cannula of FIGS. 1A-2B, wherein FIG. 3A depicts oxygen flow and FIGS. 3B and 3C depict sampling of exhaled breath.

As seen in FIG. 3A, oxygen from an oxygen source (not shown) flows through oxygen delivery tube 36, through oxygen delivery bore 16 (FIG. 2B) and exits the oral nasal sampling cannula at nasal and oral oxygen delivery openings 32 and 34, toward the nose and mouth of the subject. Oral oxygen delivery openings 34 are slightly slanted, to ensure that emitted oxygen will be directed to the mouth of the subject at least partially around the oral scoop element 22.

Turning to FIG. 3B, it is seen that breath exhaled through the subject's nose is directed through nasal prongs 18 and nasal breath collection bores 21 (FIG. 2A) toward exhaled breath collection bore 14 (FIG. 2A). In a similar manner, breath exhaled through the subject's mouth is collected in oral scoop element 22, and is directed through oral breath collection bore 26 (FIG. 2B) to exhaled breath collection bore 14. All the exhaled breath collected in exhaled breath collection bore 14 flows into exhaled breath collection tube 30, typically by means of negative pressure supplied by a pumping element (not shown) which may be connected to exhaled breath collection tube 30.

FIG. 3C shows the aerodynamic nature of internal surface 24 (FIG. 1B) of oral scoop element 22. As seen in FIG. 3C, breath exhaled from the subject's mouth hits different points on the internal surface 24 of oral scoop element 22. The multiple different flow surfaces of internal surface 24 ensure that all the exhaled breath that reaches internal surface 24 will be directed toward oral breath collection bore 26 (FIG. 2B).

It is appreciated that the importance of the use of several nasal oxygen delivery openings 32 is that during exhalation, which is the period at which the subject's exhaled breath is sampled, it is crucial that the sampled breath is substantially not diluted by the oxygen that is being delivered. In the oral nasal sampling cannula 10, the positive pressure caused by the exhalation is used to push away at least most of the oxygen from the direction of the nostril, thereby ensuring that the majority of the oxygen is not sucked into the nasal prongs 18 and does not dilute the sampled breath. The use of several nasal oxygen delivery openings 32 spreads out the pressure of the oxygen flow, and thus the exhaled air is at an even larger positive pressure relative to the pressure of the oxygen exiting each delivery opening 32, thus more effectively pushing away the oxygen.

It is appreciated that the importance of the use of an oral scoop element is in the fact that a larger percentage of the orally exhaled breath is collected and eventually reaches the sample analysis element. This feature is especially important when monitoring the breath of heavily sedated subjects, which tend to breathe through an open mouth and to have a very low breath rate, typically fewer than 10 breaths per minute, as opposed to greater than 12 breaths per minute in a non-sedated subject. Additionally, the collection of all the exhaled breath from oral scoop element 22 into the oral breath collection bore 26, which is substantially narrower than oral scoop element 22, amplifies the pressure of the orally exhaled breath, which is typically very low, specifically in sedated subjects.

Moreover, amplification of the pressure of orally exhaled breath is important for the accuracy of the sampling due to the fact that the pressure created during exhalation at the exit of a mouth which is wide open is much lower than the pressure created by the flow of exhaled breath via the nostrils.

It is also appreciated that the sampled exhaled breath is substantially not diluted by ambient air due to pressure gradients within the system, and a majority of the sampled exhaled breath does not escape from the system.

If the subject is performing oral and nasal breathing, there is a slightly higher pressure in nasal breath collection bores 21 (FIG. 2A) and in oral breath collection bore 26 (FIG. 2B), and a slightly more negative pressure in exhaled breath collection bore 14 (FIGS. 1B-2B) due to the suctioning pump which is connected to exhaled breath collection tube 30, thereby ensuring that the exhaled breath is removed from the oral nasal sampling cannula 10 and is preferably transported towards a capnograph. Due to the relatively higher pressure within the oral scoop element 22, essentially no ambient air enters breath collection bores 21 and 26 and the exhaled breath is substantially not diluted. In the case of nasal breath only, the air in oral scoop element 22 is of the same pressure as the air all around it, whereas there is a slightly higher pressure in the nasal breath collection bores 21 pushing down via the single junction 28 (FIG. 2A), to create a relatively positive pressure at the oral breath collection bore 26, thereby ensuring that essentially no ambient air will enter the oral nasal sampling cannula 10. Additionally, essentially a majority of the exhaled breath does not escape the system due to the pumping element that constantly creates a relatively negative pressure in exhaled breath collection bore 14, thereby ensuring that essentially most of the exhaled breath will travel toward the exhaled breath collection tube 30 and not out toward the ambient air.

In a similar manner, in the case of oral breath only, the air in nasal prongs 18 and in nasal breath collection bores 21 is of the same pressure as the air all around it, whereas there is a slightly higher pressure in the oral breath collection bore 26 pushing up via the single junction 28 (FIG. 2A), to create a relatively positive pressure at the nasal breath collection bores 21, thereby ensuring that essentially no ambient air will enter the system. Additionally, essentially a majority of exhaled breath does not escape the system due to the pumping element that constantly creates a relatively negative pressure in exhaled breath collection bore 26, thereby ensuring that essentially most of the exhaled breath will travel toward the exhaled breath collection tube 30 and not out toward the ambient air.

Figure 4A:
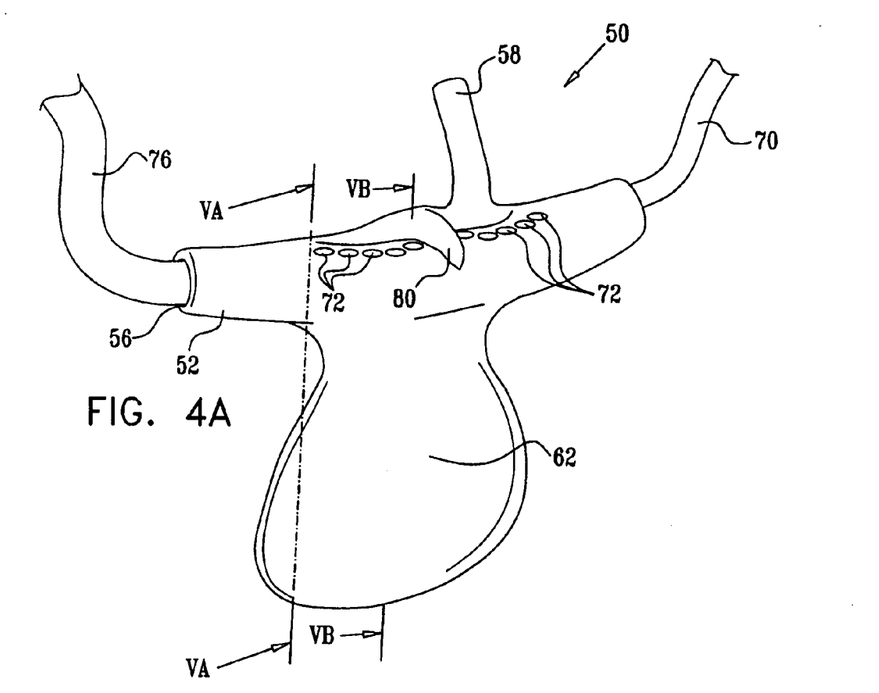
FIGS. 4A and 4B are simplified front-view and rear-view pictorial illustrations of an oral nasal sampling cannula having a single nasal prong, constructed and operative in accordance with another preferred embodiment of the present invention.
Figure 4B:
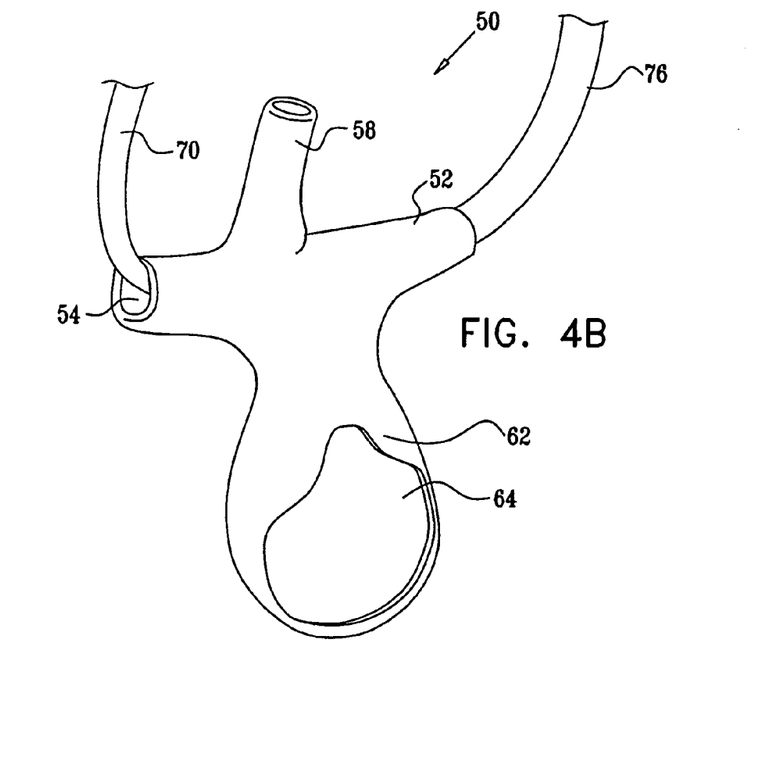
Figure 5A:
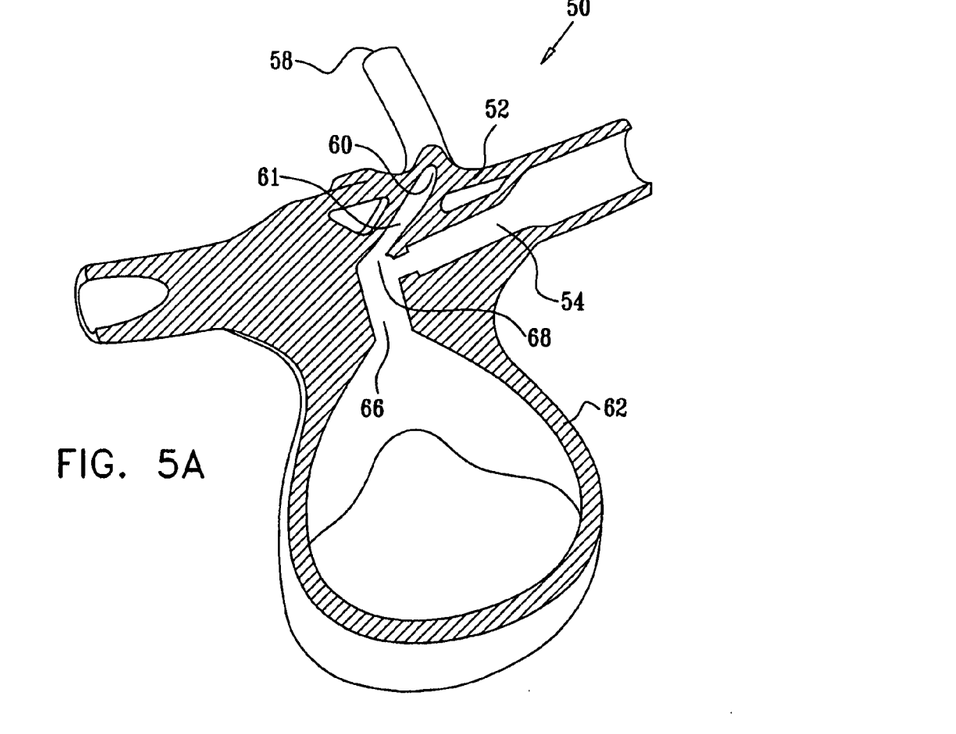
FIGS. 5A and 5B are simplified sectional illustrations taken along section lines VA-VA and VB-VB in FIG. 4A.
Figure 5B:
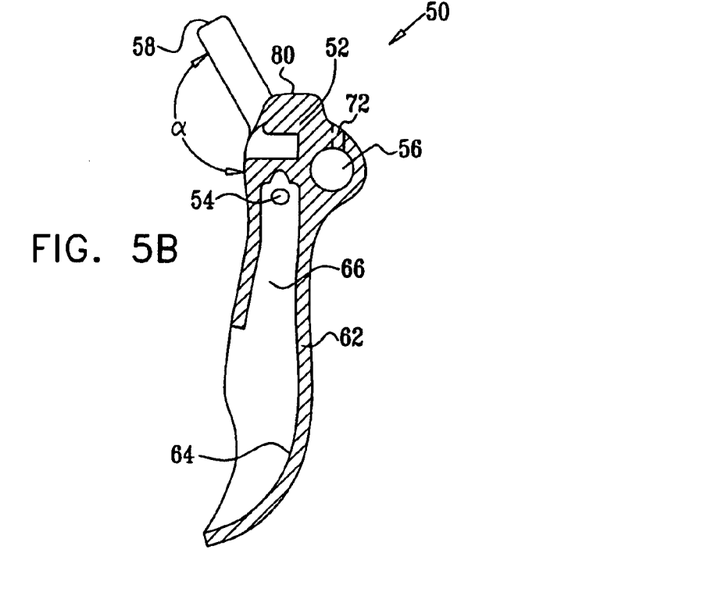

Reference is now made to FIGS. 4A and 4B, which are simplified front-view and rear-view pictorial illustrations of an oral nasal sampling cannula having a single nasal prong, constructed and operative in accordance with another preferred embodiment of the present invention and to FIGS. 5A and 5B, which are simplified sectional illustrations thereof.

FIGS. 4A-5B show an oral nasal sampling cannula 50, which is adapted for collection of gases, such as carbon dioxide, exhaled by a subject, and for supplying oxygen to the subject.

The oral nasal sampling cannula 50 comprises a main body portion 52, having formed therein an exhaled breath collection bore 54 and an oxygen delivery bore 56. A hollow nasal prong 58, having an inner end 60 which is in fluid flow communication with a nasal breath collection bore 61, is adapted for insertion into one nostril of the subject and is integrally formed with the main body portion 52.

An oral scoop element 62, including an internal surface 64, is integrally formed with main body portion 52. Oral scoop element 62 terminates at a top portion thereof in an oral breath collection bore 66, which is in fluid flow connection with nasal breath collection bore 61, thereby forming a junction 68.

Junction 68 is in fluid flow communication with exhaled breath collection bore 54, which in turn is in fluid flow communication with an exhaled breath collection tube 70, which is adapted to be connected to a suctioning pump, such as that used in a side-stream capnograph (not shown), for example Microcap®, which is commercially available from Oridion BreathID of Jerusalem, Israel.

Main body portion 52, includes, preferably at a forward facing surface thereof, or alternatively at any other suitable location, nasal oxygen delivery openings 72 which are in fluid flow communication with oxygen delivery bore 56, as seen with particular clarity in FIG. 5B. Oxygen delivery bore 56, is in fluid flow communication with an oxygen delivery tube 76, which is adapted to be connected to a source of oxygen (not shown).

Oxygen delivery tube 76 and exhaled breath collection tube 70 may optionally be placed around the ears of the subject, thereby stabilizing the oral nasal sampling cannula 50 on the subject's face.

As seen clearly in FIG. 4A, a nasal spacer 80 is integrally formed with main body portion 52 at a forward facing surface thereof. Nasal spacer 80 is adapted to engage the nose of the subject, thereby distancing the nose from nasal oxygen delivery openings 72 and ensuring that a sufficient oxygen supply reaches the subject's nose, while not closing off the subject's nasal opening, which would incur a resistance to air flow during exhalation.

Preferably, the oral nasal sampling cannula 50 is suited to the structure of a human face by having an angle, indicated by the letter a in FIG. 5B, between nasal prong 58 and oral scoop element 62. Angle α is preferably of approximately 145-165 degrees.

Figure 6A:
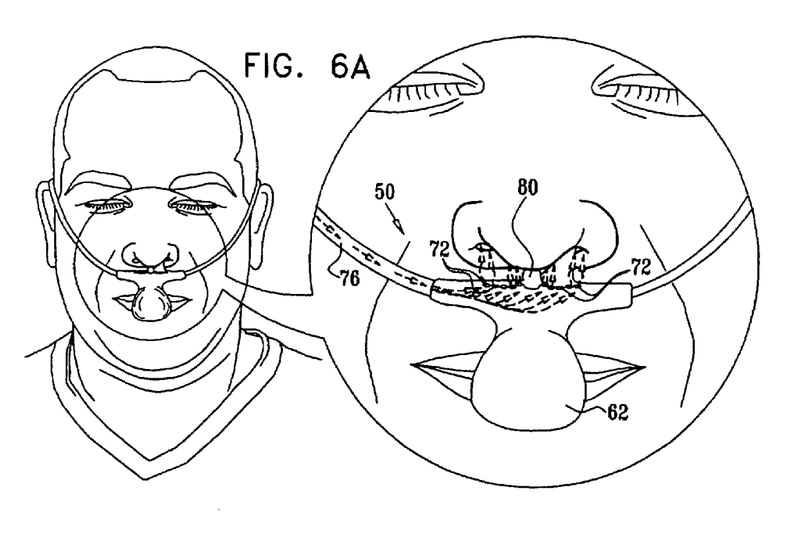
Figure 6B:
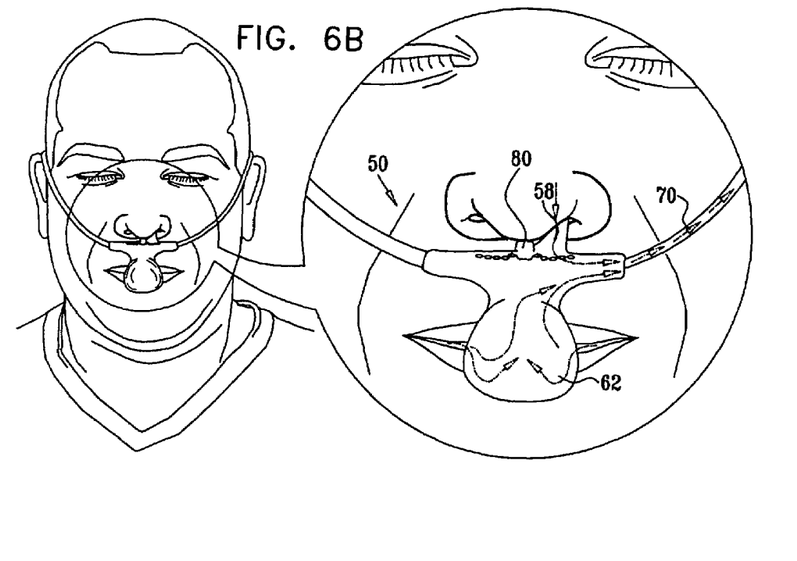
Figure 6C:
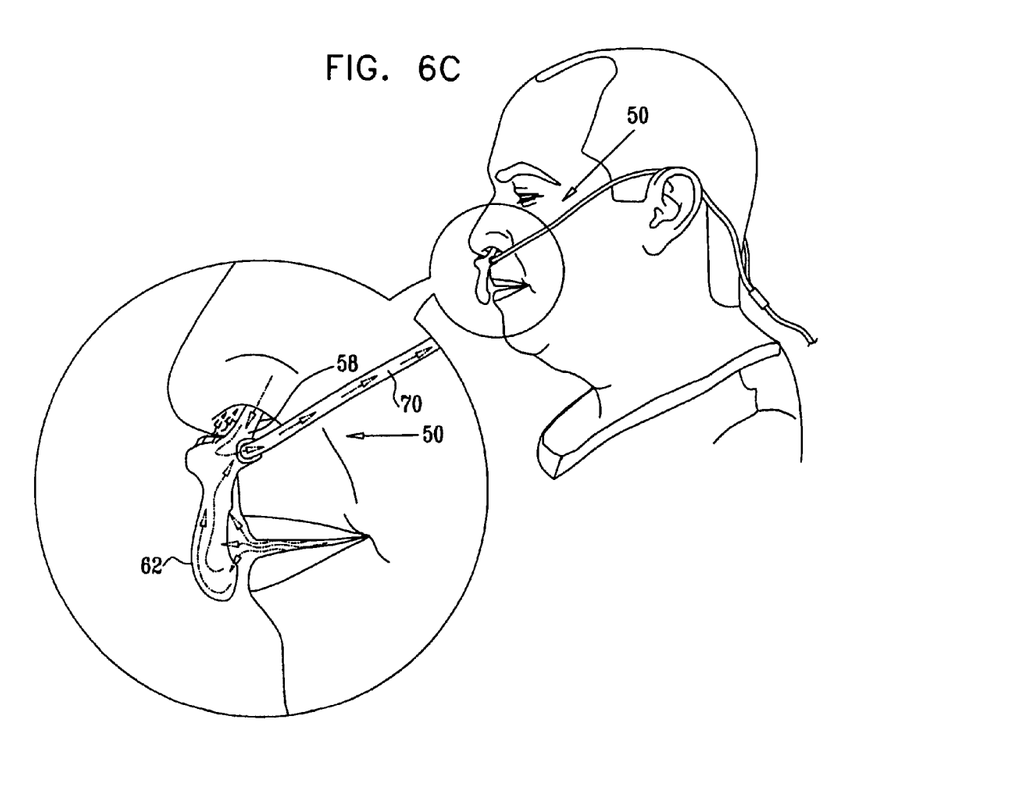

Reference is now made to FIGS. 6A, 6B and 6C, which are schematic illustrations of gas flow in the oral nasal sampling cannula of FIGS. 4A-5B, wherein FIG. 6A depicts oxygen flow and FIGS. 6B and 6C depict sampling of exhaled breath.

As seen in FIG. 6A, oxygen from an oxygen source (not shown) flows through oxygen delivery tube 76, through oxygen delivery bore 56 (FIG. 5B) and exits the oral nasal sampling cannula 50 at nasal oxygen delivery openings 72, toward the nose of the subject.

Turning to FIG. 6B, it is seen that breath exhaled through the subject's nose is directed through nasal prong 58 and nasal breath collection bore 61 (FIG. 5A) toward exhaled breath collection bore 54 (FIG. 5A). In a similar manner, breath exhaled through the subject's mouth is collected in oral scoop element 62, and is directed through oral breath collection bore 66 (FIG. 5B) to exhaled breath collection bore 54. All the exhaled breath collected in exhaled breath collection bore 54 flows into exhaled breath collection tube 70, typically by means of negative pressure supplied by a pumping element (not shown) which may be connected to exhaled breath collection tube 70.

FIG. 6C shows the aerodynamic nature of internal surface 64 (FIG. 4B) of oral scoop element 62. As seen in FIG. 6C, breath exhaled from the subject's mouth hits different points on the internal surface 64 of oral scoop element 62. The multiple different flow surfaces of internal surface 64 ensure that all the exhaled breath that reaches internal surface 64 will be directed toward oral breath collection bore 66 (FIG. 5B).

It is appreciated that the importance of the use of several nasal oxygen delivery openings 72 is that during exhalation, which is the period at which the subject's exhaled breath is sampled, it is crucial that the sampled breath is substantially not diluted by the oxygen that is being delivered. In the oral nasal sampling cannula 50, the positive pressure caused by the exhalation is used to push away at least most of the oxygen from the direction of the nostril, thereby ensuring that the majority of the oxygen is not sucked into the nasal prongs 58 and does not dilute the sampled breath. The use of several nasal oxygen delivery openings 72 spreads out the pressure of the oxygen flow, and thus the exhaled air is at an even larger positive pressure relative to the pressure of the oxygen exiting each delivery opening 72, thus more effectively pushing away the oxygen.

It is appreciated that the importance of the use of an oral scoop element is in the fact that a larger percentage of the orally exhaled breath is collected and eventually reaches the sample analysis element. This feature is especially important when monitoring the breath of heavily sedated subjects, which tend to breathe through an open mouth and to have a very low breath rate, typically fewer than 10 breaths per minute, as opposed to greater than 12 breaths per minute in a non-sedated subject.

Additionally, the collection of all the exhaled breath from oral scoop element 62 into the oral breath collection bore 66, which is substantially narrower than oral scoop element 62, amplifies the pressure of the orally exhaled breath, which is typically very low, specifically in sedated subjects.

Moreover, amplification of the pressure of orally exhaled breath is important for the accuracy of the sampling due to the fact that the pressure created during exhalation at the exit of a mouth which is wide open is much lower than the pressure created by the flow of exhaled breath via the nostril.

It is also appreciated that the sampled exhaled breath is substantially not diluted by ambient air due to pressure gradients within the system, and a majority of the sampled exhaled breath does not escape from the system.

If the subject is performing oral and nasal breathing, there is a slightly higher pressure in nasal breath collection bore 61 (FIG. 5A) and in oral breath collection bore 66 (FIG. 5B), and a slightly more negative pressure in exhaled breath collection bore 54 (FIG. 5A) due to the suctioning pump which is connected to exhaled breath collection tube 70, thereby ensuring that the exhaled breath is removed from the oral nasal sampling cannula 50 and is preferably transported towards a capnograph. Due to positive pressure within the oral scoop element, essentially no ambient air enters breath collection bores 61 and 66 and the exhaled breath is essentially not diluted.

In the case of nasal breath only, the air in oral scoop element 62 is of the same pressure as the air all around it, whereas there is slightly higher pressure in the nasal breath collection bore 61 pushing down via the junction 68 (FIG. 5A), to create a relatively positive pressure at the oral breath collection bore 66, thereby ensuring that essentially no ambient air will enter the system. Additionally, essentially most of the exhaled breath does not escape the system due to the pumping element that constantly creates a relatively low pressure in exhaled breath collection bore, thereby ensuring that essentially most of the exhaled breath will travel toward the exhaled breath collection tube 70 and not out toward the ambient air.

In a similar manner, in the case of oral breath only, the air in nasal prong 58 and in nasal breath collection bore 61 is of the same pressure as the air all around it, whereas there is a slightly higher pressure in the oral breath collection bore 66 pushing up via the junction 68, to create a relatively positive pressure at the nasal breath collection bore 61, thereby ensuring that essentially no ambient air will enter the system. Additionally, essentially a majority of the exhaled breath does not escape the system due to the pumping element that constantly creates a relatively negative pressure in exhaled breath collection bore, thereby ensuring that essentially most of the exhaled breath will travel toward the exhaled breath collection tube 70 and not out toward the ambient air.

Figure 7A:
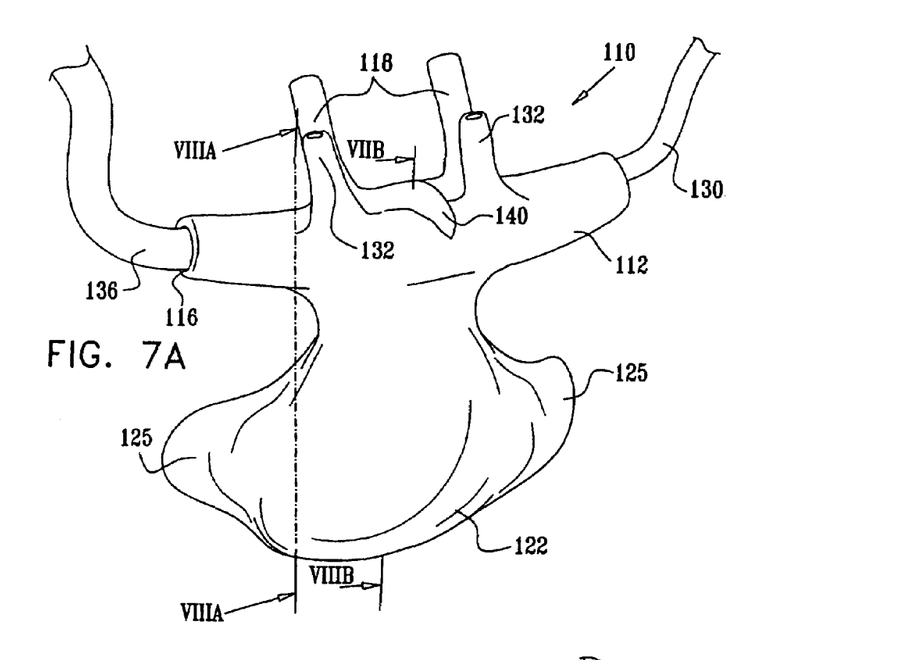
FIGS. 7A and 7B are simplified front-view and rear-view pictorial illustrations of an oral nasal sampling cannula having an enlarged oral scoop, constructed and operative in accordance with yet another preferred embodiment of the present invention.
Figure 7B:
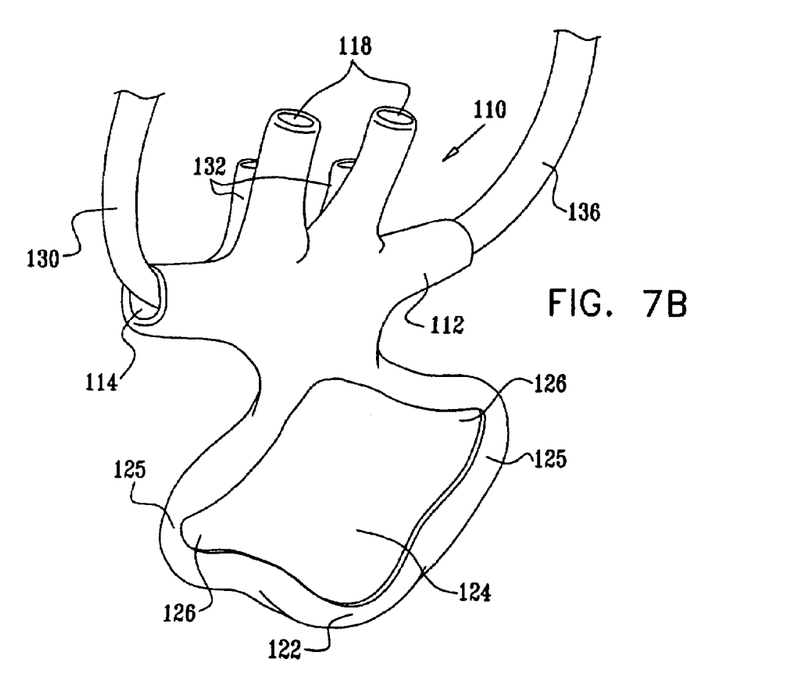
Figure 8A:
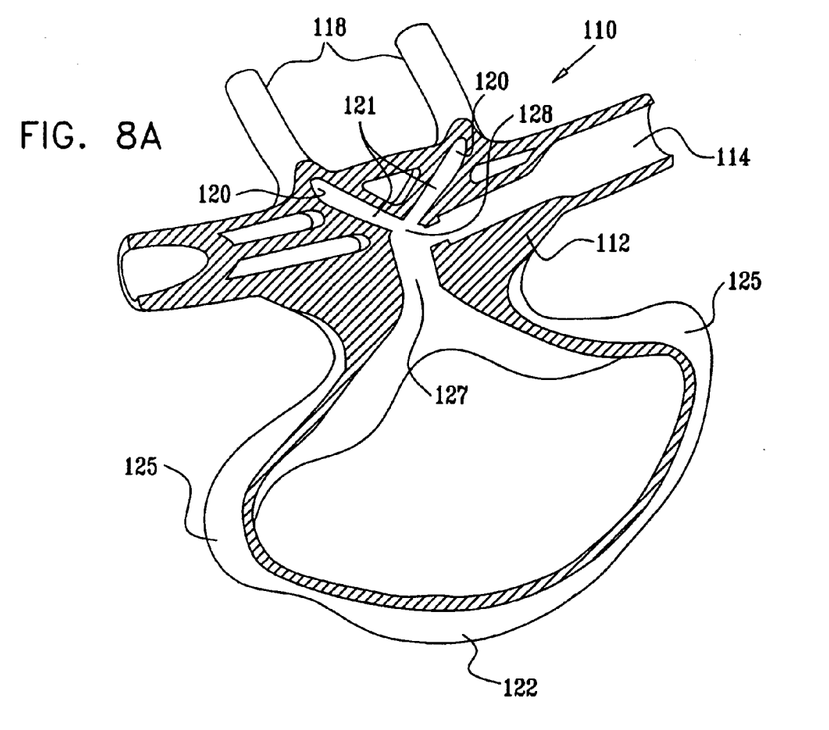
FIGS. 8A and 8B are simplified sectional illustrations taken along section lines VIIIA-VIIIA and VIIIB-VIIIB in FIG. 7A.
Figure 8B:
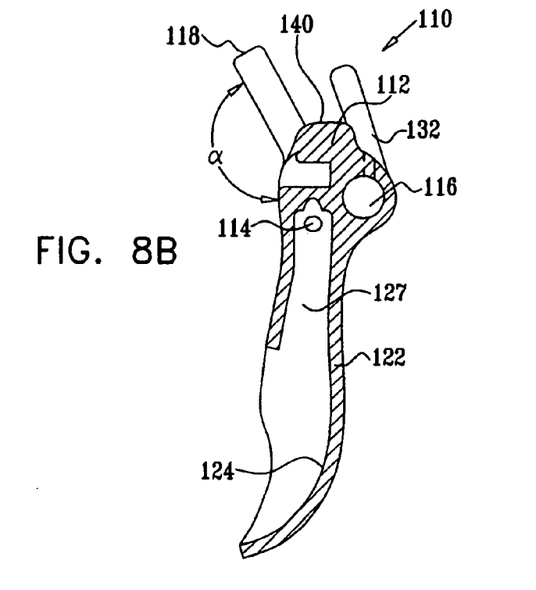

Reference is now made to FIGS. 7A and 7B, which are simplified front-view and rear-view pictorial illustrations of an oral nasal sampling cannula having an enlarged oral scoop, which is constructed and operative in accordance with a preferred embodiment of the present invention and to FIGS. 8A and 8B, which are simplified sectional illustrations thereof.

FIGS. 7A-8B show an oral nasal sampling cannula 110, which is adapted for collection of gases, such as carbon dioxide, exhaled by a subject, and for supplying oxygen to the subject.

The oral nasal sampling cannula 110 comprises a main body portion 112, having formed therein an exhaled breath collection bore 114 and an oxygen delivery bore 116. A pair of hollow nasal prongs 118, having inner ends 120, which are in fluid flow communication with a pair of nasal breath collection bores 121, is adapted for insertion into the nostrils of the subject and is integrally formed with the main body portion 112.

An oral scoop element 122, including an internal surface 124, is integrally formed with main body portion 112. Oral scoop element 122 additionally has formed thereon a pair of extension portions 125, each having an internal surface 126, and terminates at a top portion thereof in an oral breath collection bore 127. Oral breath collection bore 127 is in fluid flow connection with nasal breath collection bores 121, thereby forming a single junction 128.

Single junction 128 is in fluid flow communication with exhaled breath collection bore 114, which in turn is in fluid flow communication with an exhaled breath collection tube 130, which is adapted to be connected to a suctioning pump, such as that used in a side-stream capnograph (not shown), for example Microcap®, which is commercially available from Oridion BreathID of Jerusalem, Israel.

Main body portion 112 includes, preferably at a forward facing surface thereof or alternatively at any other suitable location, nasal oxygen delivery prongs 132 which are typically shorter than nasal prongs 118 such that they do not enter the subject's nostrils. The nasal oxygen delivery prongs 132 are in fluid flow communication with oxygen delivery bore 116, as seen with particular clarity in FIG. 8B. Oxygen delivery bore 116 is in fluid flow communication with an oxygen delivery tube 136, which is adapted to be connected to a source of oxygen (not shown).

Oxygen delivery tube 136 and exhaled breath collection tube 130 may optionally be placed around the ears of the subject, thereby stabilizing the oral nasal sampling cannula 110 on the subject's face.

As seen clearly in FIG. 7A, a nasal spacer 140 is integrally formed with main body portion 112 at a forward facing surface thereof. Nasal spacer 140 is adapted to engage the nose of the subject, thereby distancing the nostrils from nasal oxygen delivery prongs 132 and ensuring that a sufficient oxygen supply reaches the subject's nose, while not closing off the subject's nasal opening, which would incur a resistance to air flow during exhalation.

Preferably, the oral nasal sampling cannula 110 is suited to the structure of a human face by having an angle, indicated by the letter $\alpha$ in FIG. 8B, between nasal prongs 118 and oral scoop element 122. Angle $\alpha$ is preferably of approximately 145-165 degrees.

Figure 9A:
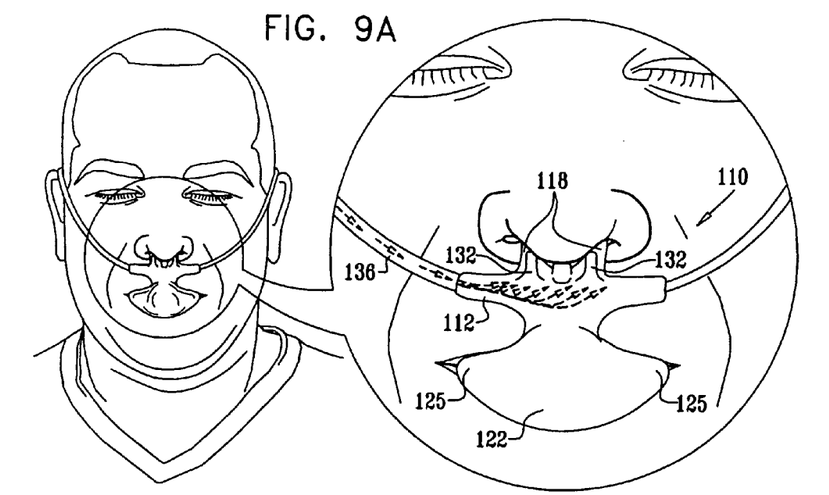
Figure 9B:
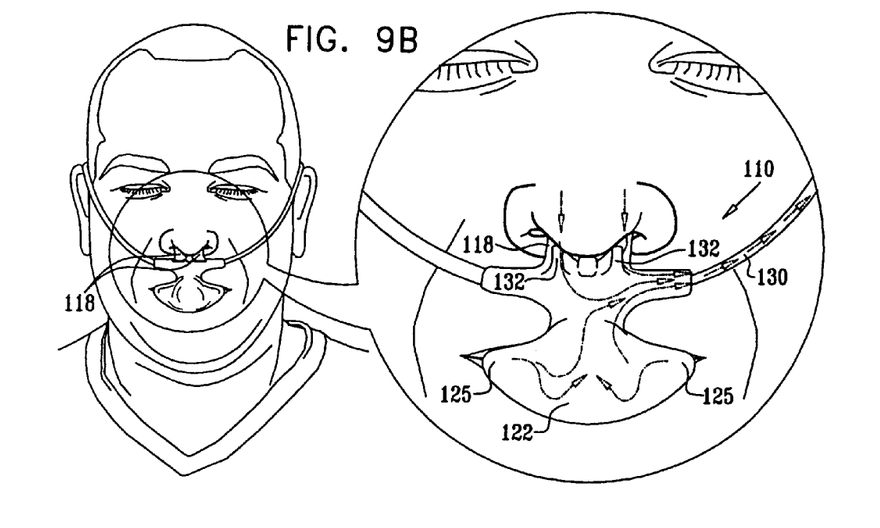
Figure 9C:
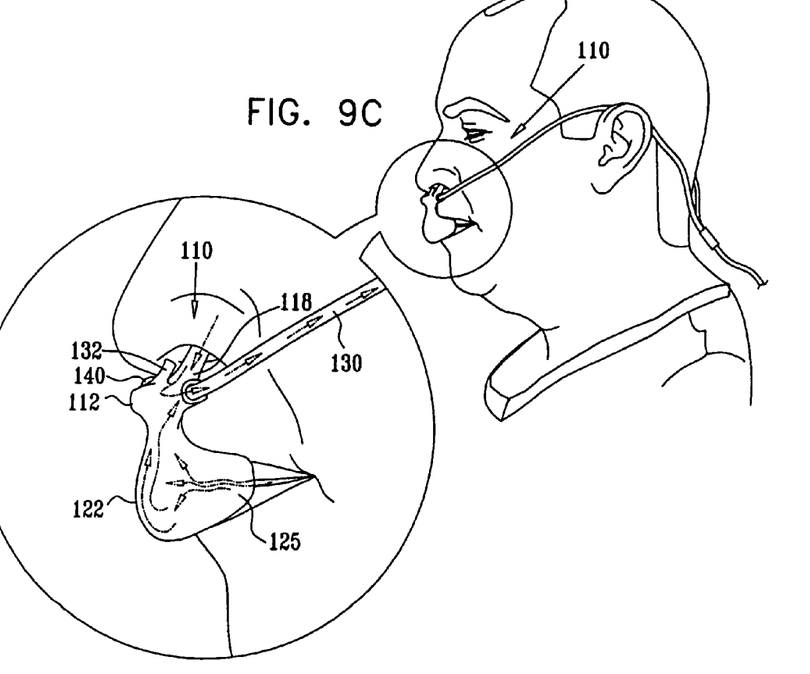

Reference is now made to FIGS. 9A, 9B and 9C, which are schematic illustrations of gas flow in the oral nasal sampling cannula 110 of FIGS. 7A-8B, wherein FIG. 9A depicts oxygen flow and FIGS. 9B and 9C depict sampling of exhaled breath.

As seen in FIG. 9A, oxygen from an oxygen source (not shown) flows through oxygen delivery tube 136, through oxygen delivery bore 116 (FIG. 8B) and exits the oral nasal sampling cannula 110 at nasal oxygen delivery prongs 132, toward the nose of the subject.

Turning to FIG. 9B, it is seen that breath exhaled through the subject's nose is directed through nasal prongs 118 and nasal breath collection bores 121 (FIG. 8A) toward exhaled breath collection bore 114 (FIG. 8A). In a similar manner, breath exhaled through the subject's mouth is collected by oral scoop element 122 and by extension portions 125, and is directed through oral breath collection bore 127 (FIG. 8B) to exhaled breath collection bore 114. All of the exhaled breath collected in exhaled breath collection bore 114 flows into exhaled breath collection tube 130, typically by means of negative pressure supplied by a pumping element (not shown) which may be connected to exhaled breath collection tube 130.

FIG. 9C shows the aerodynamic nature of internal surfaces 124 and 126 (FIGS. 7B) of oral scoop element 122 and extension portions 125 thereof. As seen in FIG. 9C, breath exhaled from the subject's mouth hits different points on the internal surfaces 124 and 126 of oral scoop element 122 and extension portions 125 thereof. The multiple different flow surfaces of internal surfaces 124 and 126 ensure that all the exhaled breath that reaches internal surfaces 124 and 126 will be directed toward oral breath collection bore 127 (FIG. 8B).

It is appreciated that the nasal oxygen delivery prongs 132 are shorter than the nasal prongs 118 such that during exhalation, which is the period at which the subject's exhaled breath is sampled, it is crucial that the sampled breath is substantially not diluted by the oxygen that is being delivered. In the oral nasal sampling cannula 110, the positive pressure caused by the exhalation is used to push away at least a majority of the oxygen from the direction of the nostril, thereby ensuring that most of the delivered oxygen is not sucked into the nasal prongs 118 and essentially does not dilute the sampled breath. If the nasal oxygen delivery prongs 132 were at the same height as the nasal prongs 118, even if the oxygen were pushed back and away during exhalation, some oxygen would still enter the sampling nasal prongs 118 thereby diluting the sample. The fact that the nasal oxygen delivery prongs 132 are lower than sampling nasal prongs 118 prevents this from occurring.

It is appreciated that the importance of the use of an oral scoop element is in the fact that a larger percentage of the orally exhaled breath is collected and eventually reaches the sample analysis element. The use of extension portions 125 ensures that generally an oral breath collection device covers a majority of the subject's mouth, thereby collecting most of the subject's orally exhaled breath. These features are especially important when monitoring the breath of heavily sedated subjects, which tend to breathe through an open mouth and to have a very low breath rate, typically fewer than 10 breaths per minute, as opposed to greater than 12 breaths per minute in a non-sedated subject.

Additionally, the collection of most of the exhaled breath from oral scoop element 122 and extension portions 125 into the oral breath collection bore 127, which is substantially narrower than oral scoop element 122 and extension portions 125 thereof, amplifies the pressure of the orally exhaled breath, which is typically very low, specifically in sedated subjects.

Moreover, amplification of the pressure of orally exhaled breath is important for the accuracy of the sampling due to the fact that the pressure created during exhalation at the exit of a mouth which is wide open is much lower than the pressure created by the flow of exhaled breath via the nostrils.

It is also appreciated that the sampled exhaled breath is substantially not diluted by ambient air due to pressure gradients within the system, and a majority of the sampled exhaled breath does not escape from the system.

If the subject is performing oral and nasal breathing, there is slightly higher pressure in nasal breath collection bores 121 (FIG. 8A) and in oral breath collection bore 127 (FIG. 8B), and slightly more negative pressure in exhaled breath collection bore 114 (FIG. 8A) due to the suctioning pump which is connected to exhaled breath collection tube 130, thereby ensuring that at least most of the exhaled breath is removed from the oral nasal sampling cannula 110 and is preferably transported towards a capnograph. Due to the relatively positive pressure within the oral scoop element 122, essentially no ambient air enters breath collection bores 121 and 127 and the exhaled breath is substantially not diluted.

In the case of nasal breath only, the air in oral scoop element 122 and in extension portions 125 is of the same pressure as the air all around it, whereas there is slightly higher pressure in the nasal breath collection bores 121, thereby ensuring that essentially no ambient air will enter the oral nasal sampling cannula 110. Additionally, essentially a majority of the exhaled breath does not escape the system due to the pumping element that constantly creates a relatively negative pressure in exhaled breath collection bore, thereby ensuring that most of the exhaled breath will travel toward the exhaled breath collection tube 130 and not out toward the ambient air.

In a similar manner, in the case of oral breath only, the air in nasal prongs 118 and in nasal breath collection bores 121 is of the same pressure as the air all around it, whereas there is slightly higher pressure in the oral breath collection bore 127 pushing up via the single junction 128, to create a relatively positive pressure at the nasal breath collection bores 121, thereby ensuring that essentially no ambient air will enter the oral nasal sampling cannula 110. Additionally, essentially a majority of the exhaled breath does not escape the system due to the pumping element that constantly creates a relatively negative pressure in exhaled breath collection bore, thereby ensuring that most of the exhaled breath will travel toward the exhaled breath collection tube 130 and not out toward the ambient air.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. An oral nasal cannula for sampling breath of a subject, comprising:
   a main body portion, having formed therein a suction port which is adapted to be connected to a suction device for side sampling of exhaled breath of said subject;
   at least one nasal prong integrally formed with said main body portion, adapted to collect nasally exhaled breath of said subject, and in fluid flow communication with a nasal breath collection bore; and
   an oral scoop, integrally formed with said main body portion, adapted to collect orally exhaled breath of said subject, and terminating in an oral breath collection bore,
   wherein said at least one nasal breath collection bore and said oral breath collection bore are in fluid flow communication with said suction port at a single junction within said cannula.

2. An oral nasal cannula according to claim 1 and wherein said main body portion is formed with at least one of at least one oral oxygen delivery port and at least one nasal oxygen delivery port.

3. An oral nasal cannula according to claim 2 and wherein said at least one nasal oxygen delivery port comprises a plurality of oxygen delivery holes formed in said main body portion.

4. An oral nasal cannula according to claim 2 and wherein said at least one nasal oxygen delivery port comprises at least one oxygen delivery prong which is integrally formed with said main body portion, which is shorter than said at least one nasal prong and is adapted to be inserted into a nostril of said subject.

5. An oral nasal cannula according to claim 2 and also comprising a nasal spacer, adapted to distance said at least one nasal oxygen delivery port from the nose of said subject when said oral nasal cannula is placed on the face of said subject.

6. An oral nasal cannula according to claim 2 and wherein said at least one oral oxygen delivery port is formed over said oral scoop.

7. An oral nasal cannula according to claim 6 and wherein said at least one oral oxygen delivery port is directed sideways, such that delivered oxygen is directed around said oral scoop.

8. An oral nasal cannula according to claim 1 and wherein said oral scoop comprises an inner surface which is configured to direct breath, exhaled from the mouth of said subject in substantially any direction, toward said suction port.

9. An oral nasal cannula according to claim 8, and wherein said inner surface comprises a plurality of flow surfaces each having a different flow direction.

10. An oral nasal cannula according to claim 1, and wherein said oral scoop covers substantially a majority of the mouth of said subject when said oral nasal cannula is placed on the face of said subject.

11. An oral nasal cannula according to claim 10 and wherein said oral scoop comprises an inner surface which is configured to direct breath, exhaled from the mouth of said subject in substantially any direction, toward said suction port.

12. An oral nasal cannula according to claim 11, and wherein said inner surface comprises a plurality of flow surfaces each having a different flow direction.

13. An oral nasal cannula according to claim 10, and being formed with an angle between said at least one nasal prong and said oral scoop.

14. An oral nasal cannula according to claim 13 and wherein said angle is in the range of 145-165 degrees.

15. An oral nasal cannula according to claim 1, and being formed with an angle between said at least one nasal prong and said oral scoop.

16. An oral nasal cannula according to claim 15 and wherein said angle is in the range of 145-165 degrees.

17. An oral nasal cannula according to claim 1 and wherein said oral scoop has an internal surface adapted to direct substantially all of said orally exhaled breath into said oral breath collection bore.

18. An oral nasal cannula according to claim 1 and wherein said oral breath collection bore is substantially narrower than said oral scoop, such that the pressure of said orally exhaled breath is amplified in said oral breath collection bore.

19. An oral nasal cannula according to claim 1 and wherein said single junction joining said at least one nasal breath collection bore and said oral breath collection bore is adapted to ensure generation of a pressure above ambient at said junction, such that during nasal breathing, the inflow of ambient air through said oral scoop is substantially prevented.

20. An oral nasal cannula according to claim 1 and wherein said single junction joining said at least one nasal breath collection bore and said oral breath collection bore is adapted to ensure generation of a pressure above ambient at said junction, such that during oral breathing, the inflow of ambient air through said at least one nasal prong is substantially prevented.

* * * * *